(12) United States Patent
Mannello et al.

(10) Patent No.: US 8,916,201 B2
(45) Date of Patent: Dec. 23, 2014

(54) CONTROLLED-RELEASE GRANULAR COMPOSITIONS CONTAINING MESALAZINE AND PROCESS FOR THE MANUFACTURE THEREOF

(75) Inventors: Antonio Mannello, Milan (IT); Carla Labruzzo, Milan (IT)

(73) Assignee: Sofar SpA, Milan (IT)

( * ) Notice: Subject to any disclaimer, the term of this patent is extended or adjusted under 35 U.S.C. 154(b) by 0 days.

(21) Appl. No.: 13/388,749

(22) PCT Filed: Jul. 21, 2010

(86) PCT No.: PCT/IB2010/053329
§ 371 (c)(1),
(2), (4) Date: Feb. 3, 2012

(87) PCT Pub. No.: WO2011/015964
PCT Pub. Date: Feb. 10, 2011

(65) Prior Publication Data
US 2012/0141592 A1    Jun. 7, 2012

(30) Foreign Application Priority Data
Aug. 6, 2009  (IT) .............................. MI2009A1434

(51) Int. Cl.
*A61K 9/14*    (2006.01)
*A61K 9/16*    (2006.01)
*A61K 9/50*    (2006.01)
*A61K 31/196*  (2006.01)

(52) U.S. Cl.
CPC ............ *A61K 9/5026* (2013.01); *A61K 31/196* (2013.01); *A61K 9/5078* (2013.01)
USPC ........................ 424/489; 424/490; 424/494

(58) Field of Classification Search
CPC ............................. A61J 31/606; A61K 31/606
See application file for complete search history.

(56) References Cited

U.S. PATENT DOCUMENTS

| 5,026,560 A * | 6/1991 | Makino et al. ................. 424/494 |
| 5,824,339 A * | 10/1998 | Shimizu et al. ............... 424/466 |
| 2003/0180352 A1* | 9/2003 | Patel et al. ..................... 424/465 |
| 2004/0170680 A1* | 9/2004 | Oshlack et al. ............... 424/457 |
| 2006/0210631 A1* | 9/2006 | Patel et al. .................... 424/470 |

FOREIGN PATENT DOCUMENTS

| IT | WO 01/66094 | * | 9/2001 |
| WO | 01/68058 A1 | | 9/2001 |
| WO | 2006/130703 A2 | | 12/2006 |
| WO | 2009/114773 A2 | | 9/2009 |

OTHER PUBLICATIONS

Rachmilewitz (BMJ 1989, 298, 82-86) Coated mesalazine . . . .*

* cited by examiner

*Primary Examiner* — David J Blanchard
*Assistant Examiner* — Tigabu Kassa
(74) *Attorney, Agent, or Firm* — Rothwell, Figg, Ernst & Manbeck P.C.

(57) ABSTRACT

The present invention refers to controlled release granular compositions of mesalazine and their use in the treatment of inflammatory pathologies of the intestinal tract. The aforesaid granular compositions comprise: a) a central core comprising an inert substrate; b) an intermediate layer comprising mesalazine and one or more physiologically acceptable excipients; c) a gastro-resistant coating. The present invention then refers to a process for obtaining the aforesaid granular compositions.

16 Claims, 2 Drawing Sheets

Figure 1:
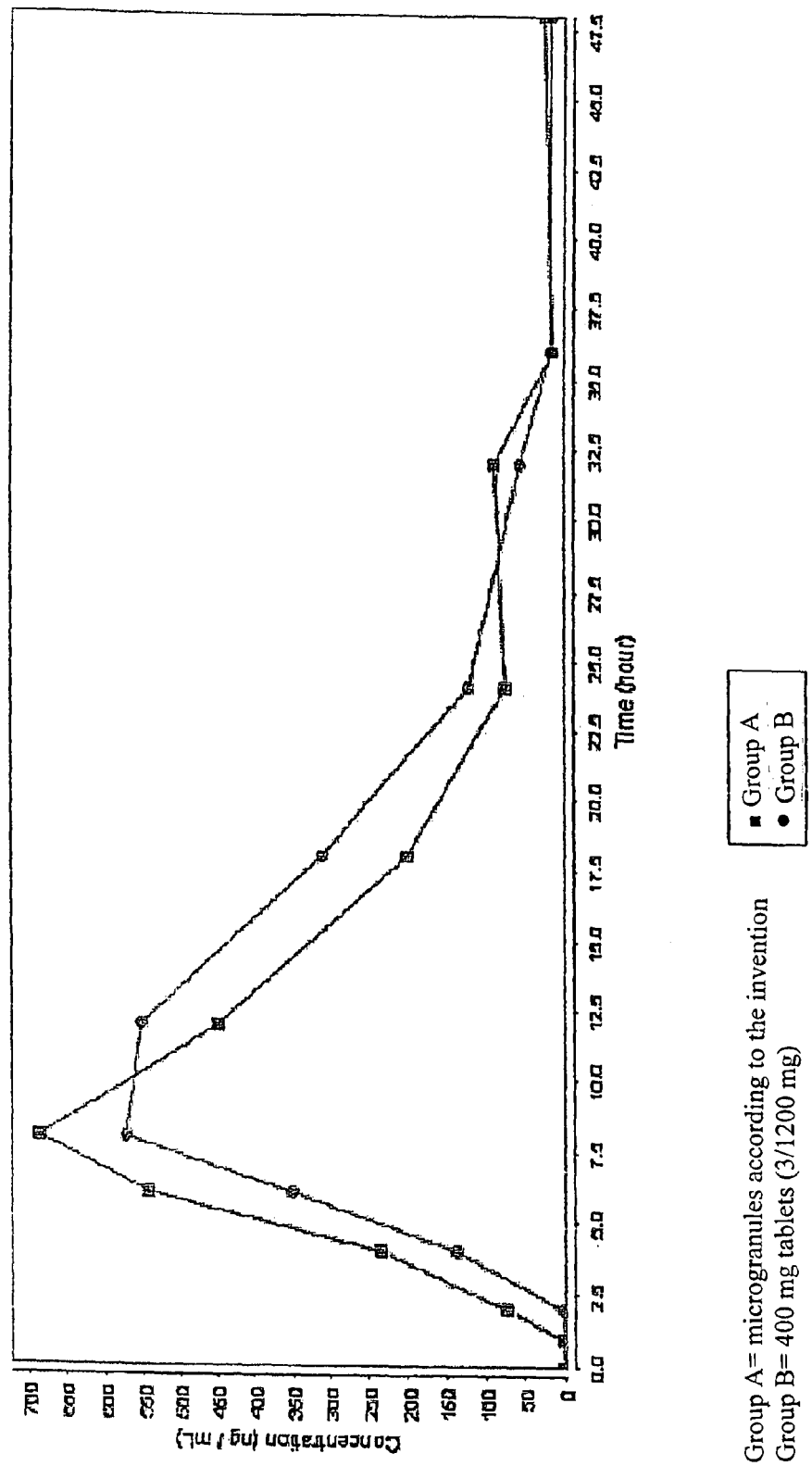

Group A= microgranules according to the invention
Group B= 400 mg tablets (3/1200 mg)

CONTROLLED-RELEASE GRANULAR COMPOSITIONS CONTAINING MESALAZINE AND PROCESS FOR THE MANUFACTURE THEREOF

CROSS-REFERENCE TO RELATED APPLICATIONS

The present application is a national stage filing under 35 U.S.C. §371 of PCT/IB2010/053329, filed on 21 Jul. 2010, and claims the benefit of priority to Italian Application MI2009A001434, filed 6 Aug. 2009, each application is incorporated herein by reference in its entirety.

DESCRIPTION

Mesalazine, or 5-aminosalicylic acid (5-ASA), is a molecule with anti-inflammatory activity, widely used for the treatment of chronic inflammatory diseases of the intestinal tract. Chronic intestinal inflammatory diseases are a group of inflammatory diseases, with acute or subtle onset, which mainly but not exclusively involve the intestine; they have chronic course and fluctuating activities and progressions over time. In this disease group, the most important are ulcerative colitis and Crohn's disease, serious and disabling diseases, which negatively affect the quality of life of the patients in addition to their health.

Ulcerative colitis is an inflammatory disease of the colon which mainly implies ulcerations and bleeding of the intestinal mucosa, strong abdominal pain and diarrhea. The disease usually has a chronic course, with acute exacerbations of the symptoms (abdominal pain, diarrhea, hematochezia, fecal urgency, anemia, weight loss, general sickness). Sometimes, the course is fulminating. The incidence of ulcerative colitis varies between 3 and 20 new cases/100,000 inhabitants each year. The most affected age range is that between 20 and 40 years old. Among the disease complications, there are also stenosis or intestinal perforation, massive hemorrhage, toxic megacolon, cancer. The complications are responsible for death within a year of disease onset in 4-6% of the subjects over 60 years old.

Crohn's disease is a chronic inflammatory disease that can be localized at any level of the oral-digestive canal. The onset age is typically between 15 and 40 years old, but it could also arise in children. The incidence in Italy is 4-5 cases/100,000 inhabitants per year (much higher in Northern Europe and in the U.S.), with a prevalence of about 52 cases/100,000 inhabitants. The most frequently affected tract is the terminal ileum and the first tract of the colon. The inflammatory process affects the entire intestinal wall; it can also cause complications for the adjacent organs. Remote effects can also be associated thereto, of autoimmune type, for example on the skin, eyes and articulations. The most common local complication is represented by the intestinal occlusion; in some cases, the resection of an intestinal tract is necessary. Overall, the disease leads to a mortality that is about twice that of the reference population.

Even though the action mechanism of mesalazine is not yet completely known, it is known that it acts locally, reducing inflammatory processes.

Mesalazine is normally administered orally or rectally; in particular, most of the oral compositions currently present on the market are formulated in tablets or granules. The oral forms currently present on the market are mainly formulated in such a manner that the active principle goes beyond the stomach, and often also beyond the small intestine, so as to be essentially released in a site-specific manner at the site of the inflammation, where it acts in a topical manner in direct contact with the mucosa.

In order to obtain such site-specificity, and the relative topical effectiveness, it is known that the oral forms of mesalazine are coated by one or more layers which allow controlling its release.

The tablets, or granules, currently present on the market are therefore prepared from a central core of mesalazine, on which the external coating is applied which ensures the control of the release and/or the gastro-resistance. The active principle therefore constitutes, up to now, the core of the formulations, which is subsequently coated.

It is extremely important to ensure the maximum compliance of the patient to the treatment with mesalazine because, for example, patients with ulcerative colitis who are not adherent to the treatment have a risk of relapse of over five times that of patients with greater compliance. The increase of the disease activity has a negative impact not only on the health of the sick patients and on their quality of life, but also leads to an increase of hospitalizations, medical visits and drug expenses for a subsequent recourse to alternative treatments that are certainly more expensive and characterized by decreased tolerability profile (e.g. systemic steroids, immunosuppressants, biological drugs).

The oral formulations of mesalazine present on the market require the consumption of a high number of tablets/granules several times a day, in order to reach a daily dosage that is optimal for the treatment. This occurs because the currently known formulation techniques do not allow the introduction of high quantities of mesalazine in the single formulations (tablet or granule) and, consequently, the repeated intake is necessary in order to reach the effective daily treatment dosage.

In order to bring about remission in patients who have distal localizations of the disease, it is also necessary to administer rectal formulations of mesalazine (foams, liquid enemas, gels, suppositories) in association with the tablets/granules. All of the above translates into complex treatment and dosage schemes, which in addition to heavily interfering with the normal daily activities of the patients, inducing non-compliance with the prescribed dosages, for example, in applications directed towards the "pediatric population", where such definition identifies the population segment from birth to eighteen years old.

The non-compliance of the patients to the treatment schemes for chronic diseases is by now widely documented and confirmed by the symptom recurrence, above all in patients with ulcerative colitis.

There is therefore the need for a simplified oral administration of mesalazine, which provides for the adaptability of the dosage to the single patient and/or the possible reduction of the number of daily consumptions, to modulate depending on the patient to be treated and on the inflammatory level present in the pathology.

It has now been surprisingly found that through a specific formulation technique, it is possible to obtain granular forms for the oral administration of mesalazine capable of releasing a high quantity of active principle in the intestinal mucosa, ensuring intake simplicity and a greater contact surface area between the active principle and the altered mucosa.

The object of the present invention therefore comprises controlled release granular oral compositions of mesalazine comprising, preferably essentially consisting of:

a) a central core comprising a substrate;

b) an intermediate layer comprising mesalazine and one or more physiologically acceptable excipients;

c) a gastro-resistant coating.

In particular, the intermediate layer b) comprises mesalazine and at least one plasticizing agent, at least one suspending agent and/or gliding agent and/or film-forming agent.

The granular compositions of the present invention therefore comprise a central core comprising a suitable substrate, on which the active principle mesalazine is applied, in turn coated with a gastro-resistant film, preferably pH-dependent.

Suitable substrates for the core of the compositions according to the present invention are preferably inert substrates, more preferably diluents, optionally with disaggregating properties. Said diluents according to the invention are preferably selected from the group that consists of microcrystalline cellulose, corn starch or a mixture thereof.

With the term "inert" according to the invention, it is intended a substrate, or core, without active principle.

Useful film-forming agents according to the invention are preferably selected from among hydroxyalkylcellulose, polyvinyl alcohol, povidone or a mixture thereof. More preferably, said film-forming agents are selected from among hydroxypropylmethylcellulose, hydroxypropylcellulose, povidone (for example, povidone K30) or a mixture thereof.

Useful plasticizers according to the invention are preferably selected from among polyalkylene glycols, glycols or a mixture thereof. More preferably, said plasticizers are selected from among polyethylene glycol 400, polyethylene glycol 6000, propylene glycol, triethyl citrate, triacetin or a mixture thereof.

Useful suspending and/or gliding agents according to the invention are preferably selected from among anhydrous colloidal silica, talc or a mixture thereof.

Useful gastro-resistant coatings according to the present invention are preferably selected from the group which consists of acrylic and methacrylic acid polymers and copolymers, polyvinyl acetate phthalate or a mixture thereof. The polyvinyl acetate phthalate according to the invention is preferably pH-dependent type.

Acrylic and methacrylic acid polymers and copolymers are for example those commonly available on the market as Eudragit®, Kollicoat MAE or a mixture thereof. Preferably, said gastro-resistant coating is the methacrylic acid copolymer type B (Eudragit S100), the methacrylic acid copolymer type C (Eudragit L100-55) or a mixture thereof.

Due to this specific formulation, which provides for the presence of the active principle mesalazine in an intermediate layer with respect to the central core, comprising a substrate and one or more physiologically acceptable excipients, and to the gastro-resistant external coating, a continuous and homogeneous release of the active principle is obtained through the entire intestinal tract, ensuring an improved pharmacological response.

In particular, the effectiveness of the compositions of the present invention is given by the fact that the active principle mesalazine is applied on an initial core, preferably an inert core, while in the known products in the art the active principle mesalazine is contained inside the initial core, which leads to a non-homogeneous release, not ensuring the complete release of the drug.

The granular form of the compositions of the invention also ensures a wider contact surface area between the active ingredient mesalazine and the target tissues, significantly contributing to obtaining an improved pharmacological response.

The topical anti-inflammatory effect of mesalazine is in fact amplified by the increased contact surface area.

The granular compositions of the invention are preferably formulated in microgranules, more preferably microgranules with dimensions comprised between 0.3 and 2.5 mm.

The mesalazine is contained in the compositions of the invention in a quantity which varies from 20 to 50% by weight, with respect to the total weight of the composition, preferably from 30 to 35%.

The substrate of the core according to the present invention is contained in the compositions in a quantity which varies from 10 to 20%, with respect to the total weight of the composition, preferably about 15%.

The gastro-resistant coating polymer according to the present invention is present in the compositions in a quantity which varies from 20 to 40%, with respect to the total weight of the composition, preferably from 25 to 35%.

The dissolution profile of the controlled release granular compositions of the invention shows a release of the active principle of less than 5% (2.6% average) in the first two hours at pH 1, and a release equal to or greater than 75% (104% average) at pH 7.5 after 45 minutes.

Due to their specific formulation, the compositions according to the present invention can get to contain high quantities of mesalazine, ensuring an improved administration compliance in which the modulation or division of the dosage is possible, as the daily administration. The term "compliance" according to the present invention is referred to the ease of adhesion of the subjects to be treated to the treatment dosage, and to the consequent greater effect of the treatment itself.

The granular compositions of the present invention are preferably obtained by means of a process which comprises one or more steps of enlargement (I) and a coating step (II).

The object of the present invention is therefore also a process for the preparation of the aforesaid granular compositions which comprises the following steps:

I) Enlargement Step:
 a) heating of the substrate in fluid bed;
 b) preparation of a suspension containing the active principle and one or more physiologically acceptable excipients;
 c) nebulization of the suspension on the substrate in a fluid bed, called spray step;
 d) drying of the product obtained in the fluid bed;
 e) cooling of the product;
 f) optional calibration of the microgranules.

Preferably, the suspension referred to in the aforesaid step b) contains mesalazine in association with at least one plasticizer, at least one suspending agent and/or gliding agent, at least one film-forming agent and at least one hydrophilic solvent, preferably water. The hydrophilic solvent is eliminated during work-up.

Useful film-forming agents according to the invention are preferably selected from among hydroxyalkylcellulose, polyvinyl alcohol, povidone (for example, povidone K30) or a mixture thereof. More preferably, they are selected from among hydroxypropylmethylcellulose, hydroxypropylcellulose, povidone (for example, povidone K30) or a mixture thereof.

Useful plasticizers according to the invention are preferably selected from among polyalkylene glycols, glycols or a mixture thereof. More preferably, said plasticizers are selected from among polyethylene glycol 400, polyethylene glycol 6000, propylene glycol, triethyl citrate, triacetin or a mixture thereof.

Useful suspending and/or gliding agents according to the invention are preferably selected from among anhydrous colloidal silica, talc or a mixture thereof.

According to a preferred embodiment of the invention, polyethylene glycol 400 (plasticizer), anhydrous colloidal silica (suspending agent), hydroxypropylmethylcellulose (film-forming agent) and purified water (solvent) are employed.

After the possible calibration step f), the possibility is provided for repeating the enlargement step in order to reach the desired granulometry and active principle percentage.

Once the desired microgranules have been obtained, the process of the present invention provides for the coating step, which in turn comprises the following steps:

II) Coating Step:

g) heating in fluid bed of the granules or microgranules obtained in the enlargement step (I);

h) preparation of a suspension containing at least one gastro-resistant coating agent and one or more further physiologically acceptable excipients;

i) nebulization of the suspension on the microgranules in the fluid bed (spray step);

j) drying of the product in the fluid bed;

k) cooling of the product.

In particular, the suspension referred to in the aforesaid step h) contains at least one gastro-resistant coating agent and at least one plasticizer, at least one suspending and/or gliding agent, at least one neutralizer and at least one hydrophilic solvent, preferably water.

The solvent and the neutralizer are eliminated during work-up.

Useful gastro-resistant coatings according to the present invention are preferably pH-dependent, more preferably selected from among acrylic and methacrylic acid polymers and copolymers, polyvinyl acetate phthalate or a mixture thereof.

According to the invention, acrylic and methacrylic acid polymers and copolymers are used such as for example, those commonly available on the market Eudragit®, Kollicoat, polyvinyl acetate phthalate pH-dependent type or a mixture thereof. Preferably, said gastro-resistant coating is the methacrylic acid copolymer type B (Eudragit S100), the methacrylic acid copolymer type C (Eudragit L100-55) or a mixture thereof.

Useful plasticizers according to the invention are preferably selected from among polyalkylene glycols, glycols or a mixture thereof. More preferably, polyethylene glycol 400, polyethylene glycol 6000, propylene glycol, triethyl citrate, triacetin or a mixture thereof.

Useful suspending and/or gliding agents according to the invention are preferably selected from among anhydrous colloidal silica, talc or a mixture thereof.

According to a preferred embodiment of the invention, methacrylate acid copolymers (gastro-resistant coating), triethyl citrate (plasticizer), anhydrous colloidal silica (suspending agent), a 30% ammonia solution (neutralizer) and purified water are employed.

At the end of the aforesaid cooling step k), the granular composition is analytically controlled and divided into sachets of weight preferably equal to about 4 grams in total, containing a quantity of mesalazine preferably equal to about 1.2 grams.

The analytical control is preferably directed to the evaluation of the active principle titer, dissolution profile and loss on drying (LOD).

In particular, the active principle titer is preferably comprised between 90 and 100%, a LOD value 5%.

Each of the above-described steps is carried out according to the invention by using a fluid bed, for example an Innojet Ventilus fluid bed.

According to one embodiment of the present invention on laboratory scale, the heating referred to in step a) of the aforesaid enlargement step (I) occurs at a temperature preferably comprised between 32 and 36° C., for a time interval preferably comprised between 10 and 60 minutes.

The spray step referred to in step c) of the step (I) occurs at a temperature of the product preferably comprised between 32 and 36° C. for a time interval sufficient for delivering the entire suspension containing the active principle.

The drying referred to in step d) of the step (I) preferably occurs at a temperature of about 40° C., for a time sufficient for obtaining humidity of less than about 5%, preferably at 2%.

The cooling referred to in step e) of step (I) is preferably carried out until reaching a temperature of the product that is less than or equal to 30° C.

The possible calibration of the granulometry referred to in step f) of step (I) is preferably carried out with an approximately 0.5 mm net.

With regard to the aforesaid coating step (II), the heating referred to in step g) occurs at a temperature of the product preferably comprised between 29 and 32° C. for a time interval preferably comprised between 10 and 60 minutes.

The spray step referred to in step i) of the step (II) preferably occurs at a temperature comprised between 29 and 32° C. for the time necessary for consuming the gastro-resistant suspension.

The drying referred to in step j) of the step (II) preferably occurs at a temperature of the product of about 40° C., for about 60 minutes, until a humidity of less than about 5% has been obtained, preferably of 2%.

The cooling referred to in step k) of step (II) is preferably carried out until the obtention of a product temperature that is less than or equal to 30° C.

The process of the present invention is essentially based on the nebulization (spray) of a suspension, containing the active principle in the aforesaid step (I), or the coating polymer in the aforesaid step (II), on a fluid bed of orbiting powder (substrate or core), maintained by a flow of constant air, thermostated at a temperature capable of allowing the formation of the granular composition of mesalazine via the simultaneous balance of wetting and drying.

Said nebulization occurs due to a rotating nozzle of particular size that exploits the pressurized air by forming microdrops (atomization) that come into contact with the above-mentioned substrate.

According to the embodiment of the invention on laboratory scale, the nebulization pressure is preferably comprised between 1 and 2 bars, while the quantity of incoming air (IN) in the different steps of the process varies from 25 to 65 m3/hour. Preferably, about 30 m3/hour in the heating step, about from 30 to 45 m3/hour in the spray step and about from 50 to 60 m3/hour in the drying. The heating in the initial steps of the steps I (a) and II (g) is therefore necessary for the prearrangement of the substrate, and of the suspension, to the subsequent nebulization step, for which a product temperature of at least 34-35° C. for step I, and 29-30° C. for step 11 must be preferably reached; it is in any case important that the value of the outgoing air temperature (out) is as close as possible to that of the product before starting the atomized supply (spray) of the suspension inside the bed, supplied by a peristaltic pump. Said peristaltic pump operates at a speed comprised between 22 and 50%.

Said nebulization (spray) occurs with a flow rate, or air flow, comprised between 30 and 45 m3/h.

The object of the present invention therefore also comprises the controlled release granular compositions obtainable through the above-described process.

Further object of the present invention are the aforesaid granular compositions for use in the treatment of the inflammatory pathologies of the intestinal tract.

The aforesaid pathologies are preferably selected from among ulcerative colitis, Crohn's disease and acute and chronic intestinal phlogosis, localized in the ileum and in the colon.

Due to the possibility to divide the dosage and the ease of deglutition, the compositions of the invention are also directed to the use in geriatric treatment and the treatment of the "pediatric population", where the definition of "pediatric population" identifies the population segment from birth to eighteen years old, e.g. in the case of child-onset Crohn's disease.

The following examples illustrate the invention in greater detail without limiting it in any manner. The quantitative values expressed in the following examples are expressed as a percentage with respect to the total weight of the composition.

EXAMPLES

Example 1

Microgranular Mesalazine Composition

|  | % |
|---|---|
| Core: | |
| microcrystalline cellulose (substrate) | 14.88 |
| Intermediate layer: | |
| mesalazine (API) | 30 |
| polyethylene glycol 400 (plasticizer) | 3.26 |
| anhydrous colloidal silica (suspending agent) | 0.79 |
| hydroxypropylmethylcellulose (film-forming agent) | 3.26 |
| Gastro-resistant coating: | |
| Eudragit S100 + Eudragit L100-55 (coating) | 31.38 |
| Triethyl citrate (plasticizer) | 15.68 |
| Anhydrous colloidal silica (suspending agent) | 0.75 |

Example 2

Microgranular Mesalazine Composition

|  | % |
|---|---|
| Core: | |
| microcrystalline cellulose (substrate) | 16.46 |
| Intermediate layer: | |
| mesalazine (API) | 35.57 |
| polyethylene glycol 400 (plasticizer) | 3.56 |
| anhydrous colloidal silica (suspending agent) | 0.75 |
| hydroxypropylmethylcellulose (film-forming agent) | 3.56 |
| Gastro-resistant coating: | |
| Eudragit S100 + Eudragit L100-55 (coating) | 26.27 |
| Triethyl citrate (plasticizer) | 13.12 |
| Anhydrous colloidal silica (suspending agent) | 0.71 |

Example 3

Obtention Process

Enlargement Step (I)

Using the Innojet ventilus 1 fluid bed, proceed to the granule enlargement step, starting from microcrystalline cellulose (Vivapur 12, central substrate) which is inserted in the fluid bed by means of a suction loading function.

Then, proceed to the heating, which prepares the substrate powder bed for the subsequent spray step (atomized supply) at a temperature between 32 and 36° C. for about 10 minutes; once the product and the outgoing air reach a temperature of about 35° C., proceed with the spraying of the suspension containing the mesalazine inside the bed, via the actuation of a peristaltic pump.

The peristaltic pump is employed in the present process at a speed comprised between 22 and 50%, while the nebulization pressure is comprised between 1 and 1.5 bars.

The spraying occurs with a flow rate or air flow comprised between 30 and 45 m3/h.

Once the suspension to be sprayed is consumed, proceed with the drying of the product at a temperature of about 40° C. for 15 minutes, with the purpose of reducing the humidity of the final product to a minimum (LOD %).

Finally, there is the cooling step of the product to about 25-30° C., which essentially consists of excluding the heating and the air recirculation.

At the end of the enlargement step, possibly proceed with a repetition of the same step in order to reach the pre-established granular size and/or titer of the active principle.

The suspension used in the enlargement step of example 2 contains:

| substance | % in suspension | function |
|---|---|---|
| Mesalazine | 18.15 | API |
| Polyethylene glycol 400 | 1.18 | Plasticizer |
| Anhydrous colloidal silica-Aerosil 200 | 0.37 | suspending agent |
| Hydroxypropylmethylcellulose-pharmacoat 615 | 1.18 | film-forming agent |
| Purified water* | q.s. to 100 | Solvent |

*eliminated during work-up

For the preparation of the above suspension, the hydroxypropylmethylcellulose is dispersed in 50% of the total purified water until complete dissolution.

In a separate container, the remaining purified water is poured and the colloidal silica and mesalazine are added under mechanical stirring for a time of 20 to 40 minutes. The above is homogenized at maximum speed until an homogeneous suspension is obtained.

Then, proceed to combine the homogeneous suspension with the solution of water and hydroxypropylmethylcellulose mentioned above, still under stirring. Continue by adding polyethylene glycol 400, always under stirring.

Finally, the obtained solution is passed through a net of about 500 μm.

The suspension thus obtained is ready to be supplied inside the fluid bed, as described above.

Coating Step (II)

The coating step occurs in a single step, so as to obtain a film that is as homogeneous as possible.

Still using the Innojet ventilus fluid bed, proceed to the final step of gastro-resistant coating of the microgranules obtained in the previous enlargement step (I). Then proceed to load the fluid bed by means of suction with 59.63% of the granules obtained in the previous step.

Then, proceed to the heating of the granules and to the subsequent spray step of the suspension containing the gastro-resistant polymer.

In the coating step, the temperature of the product does not exceed 32° C. and the nebulization pressure is equal to about 1 bar.

Also in this step, one proceeds with the drying at a product temperature of about 40° C. for 60 minutes, with the purpose of reducing the final product humidity to a minimum (LOD %).

Finally, the cooling step of the product to room temperature, which consists of excluding the heating and the air recirculation.

At the end of the entire process, one carries out the analytical control of the obtained product, evaluating the titer of active principle, the relative dissolution profile, density and loss on drying (LOD).

The suspension used in the coating step of example 2 contains:

| substance | % in suspension | function |
|---|---|---|
| Methacrylic acid copolymer-Eudragit S100 | 12.52 | gastro-resistant agent |
| Methacrylic acid copolymer-Eudragit L100-55 | 4.60 | gastro-resistant agent |
| Triethyl citrate | 6.48 | plasticizer |
| Anhydrous colloidal silica-Aerosil 200 | 0.37 | suspending agent |
| 30% Ammonia* | 0.47 | neutralizer |
| Purified water* | q.s. to 100 | solvent |

*eliminated during work-up

For the preparation of the above suspension, proceed with the solubilization of the ammonia solution in 10% of the total purified water until complete dissolution. In a separate container, 55% of the total purified water is poured and Eudragit S100 is dispersed for about 10 minutes.

Then, add 97.5% of the above ammonia solution under stirring to the solution containing the Eudragit S100, and continue stirring for at least 60 minutes. In a suitable container, Eudragit L100-55 is dispersed in 2.5% of the purified water and the remaining part of the above ammonia solution is added. The stirring continues for at least 60 minutes.

In another container, the anhydrous colloidal silica is dispersed in 32.5% of the total purified water and is homogenized for about 2 minutes.

Finally, the phases containing Eudragit S100 and Eudragit L100-55 are added under stirring, combining the dispersion containing colloidal silica.

The triethyl citrate is slowly added to the total, far away from the stirrer. The stirring continues for at least another hour.

The obtained suspension is then passed through a net of about 500 μm.

The suspension thus obtained is ready to be supplied inside the fluid bed, as described above.

Experimental Part

Bioequivalence was verified between the granular composition of example 1 and controlled release tablets of mesalazine 400 mg available on the market (reference formulation).

First, therefore, an in vitro test was carried out in order to evaluate the dissolution kinetics of the composition of the invention with respect to the reference composition, the latter being represented by 3 tablets of 400 mg mesalazine (1200 mg total) found on the market.

The percentage of release of the active principle from the reference composition was 0% at pH 1 after 2 hours and 70%±5% at pH 7.5 after 45 minutes.

The percentage of release of the active principle from the composition of the invention (example 1) was 0% at pH 1 after 2 hours and 78%±3% at pH 7.5 after 45 minutes.

Such data therefore shows that the in vitro dissolution ratio of mesalazine for the composition of the invention is greater than that of the reference composition (tablets).

A study of 23 healthy volunteers was conducted in order to verify the plasmatic levels of non-modified mesalazine (5-ASA) and of the relative metabolite N-acetyl-5-ASA.

The study provided for the random administration of three 400 mg tablets of mesalazine in a single administration (for a total of 1200 mg of active principle) to 11 patients, evaluated with respect to the administration to 13 patients of a sachet of microgranules containing 1200 mg of mesalazine (example 1) according to the present invention (example 1).

The dose of the reference formulation was adapted in a such manner to test the same dosage as the composition of the invention.

All the patients were subjected to drawing 8 ml of blood at time 0 (immediately before the administration of the drug), 1 h, 2 h, 4 h, 6, 8 h, 12, 18 h, 24 h, 32 h and 48 h after the administration. The samples were then centrifuged at 2000 revolutions for 10 minutes and the resulting fractions of plasma were frozen at −80° C. until the moment of analysis.

The results of the study demonstrated the bioequivalence of the two mesalazine formulations, measured in terms of primary variables with respect to the plasmatic concentration value of mesalazine and/or its metabolite N-acetyl-5-ASA in the time AUC (0-t)(0-∞), and maximum concentration of the active principle and/or its metabolite N-acetyl-5-ASA in the plasma ($C_{max}$) by means of the ANOVA method (tables 1 and 2). The bioequivalence of the two formulations was finally evaluated by means of the Schuirmann "t" test.

TABLE 1

Summary statistics of the pharmacokinetic parameters of 5-ASA for treatment (population).

| | | Microgranules (n = 23) | Tablets (n = 23) |
|---|---|---|---|
| Cmax | Mean (±S.D.) (ng/ml) | 795 (±363) | 835 (±557) |
| | Min-Max (mg/ml) | 265-1350 | 240-1480 |
| | Coefficient of variation (%) | 45.6 | 66.7 |
| | Geometric mean (ng/ml) | 700 | 689 |
| tmax | Mean (±S.D.) (h) | 8.1 (±1.4) | 10.6 (±4.3) |
| | Min-Max (h) | 6.0-12.0 | 6.0-18.0 |
| | Coefficient of variation (%) | 17.5 | 40.4 |
| | Geometric mean (h) | 8.0 | 9.9 |
| AUC0-t | Media (±S.D.) (ng · h/ml) | 9060 (±4170) | 9180 (±4040) |
| | Min-Max (ng · h/ml) | 3570-23120 | 3490-27340 |
| | Coefficient of variation (%) | 46.1 | 53.9 |
| | Geometric mean (h) | 8070 | 8070 |
| AUC0-∞ | Mean (±S.D.) (ng · h/ml) | 9490 (±4120) | 9380 (±4950) |
| | Min-Max (ng · h/ml) | 4250-22040 | 4370-25990 |
| | Coefficient of variation (%) | 43.4 | 52.7 |

TABLE 1-continued

Summary statistics of the pharmacokinetic
parameters of 5-ASA for treatment (population).

|  |  | Microgranules (n = 23) | Tablets (n = 23) |
|---|---|---|---|
|  | Geometric mean (h) | 8550 | 8260 |
| $t^{1/2}$ | Mean (±S.D.) (h) | 8.0 (±6.0) | 6.0 (±3.8) |
|  | Min-Max (ng · h/ml) | 2.3-18.2 | 2.4-15.3 |
|  | Coefficient of variation (%) | 74.9 | 63.9 |
|  | Geometric mean (h) | 6.5 | 5.1 |

TABLE 2

Summary statistics of the pharmacokinetic
parameters of N-Acetyl-5-ASA for treatment (population).

|  |  | Microgranules (n = 23) | Tablets (n = 23) |
|---|---|---|---|
| Cmax | Mean (±S.D.) (ng/ml) | 1554 (±612) | 1471 (±585) |
|  | Min-Max (mg/ml) | 762-3290 | 802-3110 |
|  | Coefficient of variation (%) | 39.4 | 39.8 |
|  | Geometric mean (ng/ml) | 1460 | 1378 |
| Tmax | Mean (±S.D.) (h) | 8.0 (±1.5) | 11.5 (±4.5) |
|  | Min-Max (h) | 6.0-12.0 | 6.0-24.0 |
|  | Coefficient of variation (%) | 18.5 | 39.4 |
|  | Geometric mean (h) | 7.9 | 10.7 |
| AUC0-t | Mean (±S.D.) (ng · h/ml) | 28120 (±7820) | 28770 (±9770) |
|  | Min-Max (ng · h/ml) | 13430-48170 | 13550-56650 |
|  | Coefficient of variation (%) | 27.8 | 34.0 |
|  | Geometric mean (h) | 27030 | 27246 |
| AUC0-∞ | Mean (±S.D.) (ng · h/ml) | 33190 (±8830) | 34500 (±13730) |
|  | Min-Max (ng · h/ml) | 15270-50980 | 13550-74600 |
|  | Coefficient of variation (%) | 26.6 | 39.8 |
|  | Geometric mean (h) | 31950 | 32060 |
| $t^{1/2}$ | Mean (±S.D.) (h) | 15.6 (±7.2) | 14.2 (±6.9) |
|  | Min-Max (ng · h/ml) | 2.4-36.1 | 2.4-24.8 |
|  | Coefficient of variation (%) | 46.5 | 48.4 |
|  | Geometric mean (h) | 13.9 | 12.2 |

Figure 2:
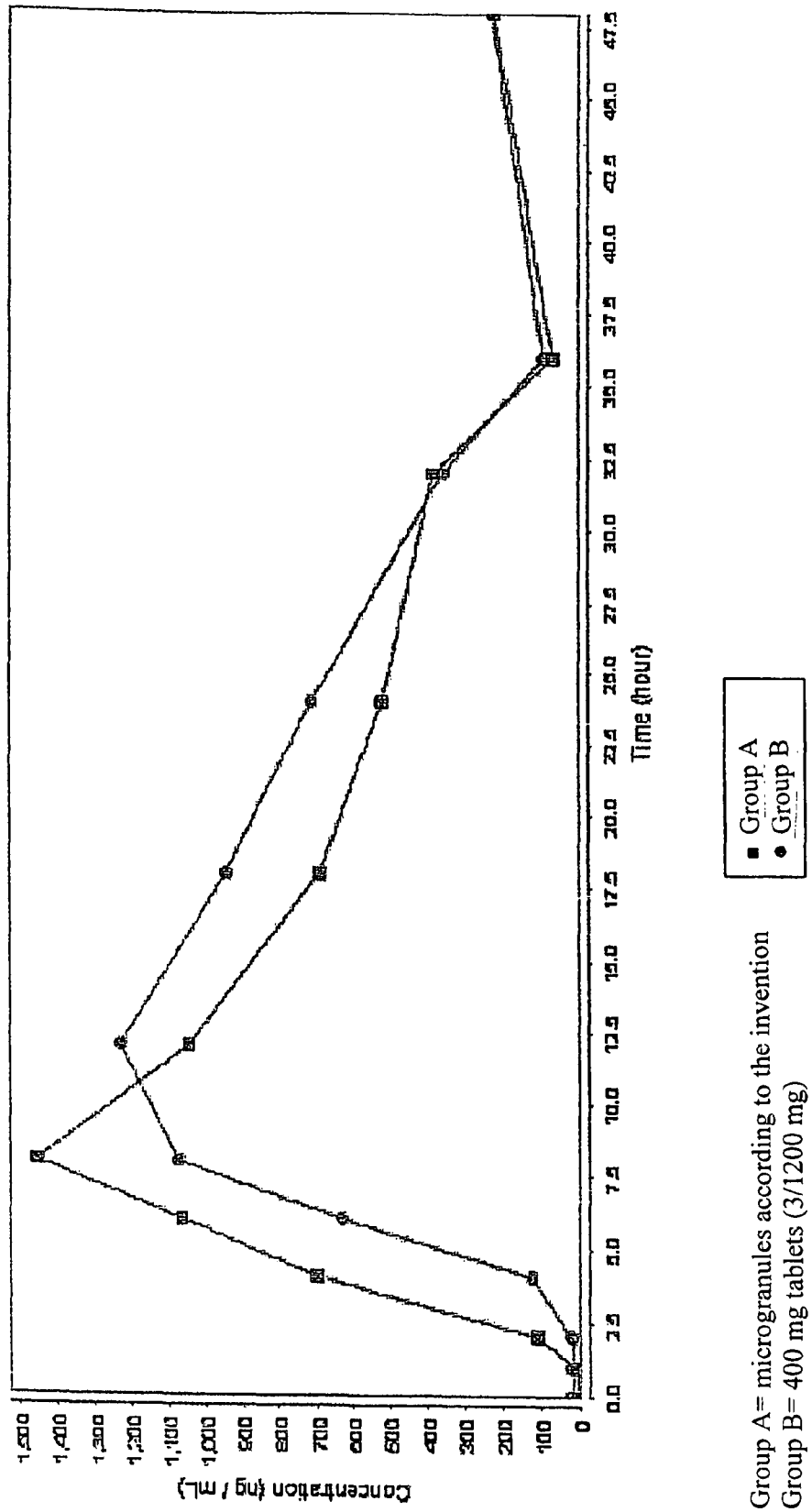

The graphs A and B, respectively reported in FIG. 1 and in FIG. 2, show the obtained results in greater detail.

In addition, the pharmacokinetics study has shown a faster plasmatic appearance of mesalazine (5-ASA) after the granular administration of the invention (tmax of 8.1 hours), with respect to that shown after the administration of mesalazine in the reference tablets (tmax 10.6 hours). The values of Cmax and AUC resulted similar for both formulations and the plasmatic disappearance kinetics of the tested composition were slightly faster.

The variability between subjects was shown to be lower after the administration of the composition of the invention, with a % CV of about 17.5%, with respect to the 40.4% of the reference tablets; this is due to the more homogeneous controlled release of the granular form according to the invention.

The metabolite N-acetil-5-ASA has a plasmatic profile similar to mesalazine in both compositions.

The use of the granular composition of the invention is therefore safe and allows reducing daily dosages, improving the treatment compliance.

The invention claimed is:

1. A granular composition with controlled release of mesalazine comprising:
    a) a central core consisting of an inert substrate, wherein the inert substrate is microcrystalline cellulose and wherein said core contains 14.88% by weight of the microcrystalline cellulose with respect to the total weight of the composition;
    b) an intermediate layer comprising mesalazine, a plasticizer, a suspending agent and/or gliding agent and a film-forming agent, wherein the plasticizer is a polyalkylene glycol, the suspending agent and/or gliding agent is silicone dioxide and the film forming agent is a hydroxyalkylcellulose and wherein said intermediate layer b) contains 30% by weight of mesalazine, 3.26% by weight of polyethylene glycol 400, 0.79% by weight of colloidal silicon dioxide, 3.26% by weight of hydroxypropylmethylcellulose with respect to the total weight of the composition; and
    c) a gastro-resistant coating selected from among methacrylic and acrylic acid polymers and copolymers, wherein said gastro-resistant coatig c) contains 31.38% by weight of methacrvlic acid copolymer, 15.68% by weight of triethyl citrate and 0.75% by weight of colloidal silicon dioxide, with respect to the total weight of the composition.

2. The granular composition according to claim 1, wherein said gastro-resistant coating is a methacrylic acid copolymer type B, methacrylic acid copolymer type C or a mixture thereof.

3. The granular composition according to claim 1, having particle dimensions comprised between 0.3 and 2.5 mm.

4. The granular composition according to claim 1, in microgranular form.

5. A granular composition with controlled release of mesalazine comprising:
    a) a central core consisting of an inert substrate, wherein the inert substrate is microcrystalline cellulose and wherein said core contains 16.46% by weight of the microcrystalline cellulose with respect to the total weight of the composition;
    b) an intermediate layer comprising mesalazine, a plasticizer, a suspending agent and/or gliding agent and a film-forming agent, wherein the plasticizer is a polyalkylene glycol, the suspending agent and/or gliding agent is silicone dioxide and the film forming agent is a hydroxyalkylcellulose and wherein said intermediate layer b) contains 35.37% by weight of mesalazine, 3.56% by weight of polyethylene glycol 400, 0.75% by weight of colloidal silicon dioxide, 3.56% by weight of hydroxypropylmethylcellulose with respect to the total weight of the composition; and
    c) a gastro-resistant coating selected from among methacrylic and acrylic acid polymers and copolymers, wherein said gastro-resistant coating c) contains 26.27% by weight of methacrylic acid copolymer, 13.2% by weight of triethyl citrate and 0.71% by weight of colloidal silicon dioxide, with respect to the total weight of the composition.

6. The granular composition according to claim 1 for use in the treatment of inflammatory pathologies of the intestinal tract.

7. The granular composition according to claim 6, for the treatment of ulcerative colitis, of Crohn's disease and of acute or chronic phlogosis.

8. The granular composition according to claim 1, for the treatment of the pediatric population.

9. The granular composition according to claim 1 obtainable according to a process which comprises the following passages:
 a) heating of a substrate in a fluid bed;
 b) preparation of a suspension containing the active principle and one or more physiologically acceptable excipients;
 c) nebulization of the suspension on the substrate in the fluid bed;
 d) drying of the product obtained in the fluid bed;
 e) cooling of the product;
 f) optional calibration of the granules or microgranules;
 g) application of a gastro-resistant coating.

10. The granular composition according to claim 5, wherein said methacrylic acid copolymer is a mixture of methacrylic acid copolymer type B and methacrylic acid copolymer type C.

11. The granular composition according to claim 5, having particle dimensions comprised between 0.3 and 2.5 mm.

12. The granular composition according to claim 5, in microgranular form.

13. The granular composition according to claim 5 for the treatment of inflammatory pathologies of the intestinal tract.

14. The granular composition according to claim 13, for the treatment of ulcerative colitis, of Crohn's disease and of acute or chronic phlogosis.

15. The granular composition according to claim 5, for the treatment of the pediatric population.

16. The granular composition according to claim 5 obtainable according to a process which comprises the following passages:
 a) heating of a substrate in a fluid bed;
 b) preparation of a suspension containing the active principle and one or more physiologically acceptable excipients;
 c) nebulization of the suspension on the substrate in the fluid bed;
 d) drying of the product obtained in the fluid bed;
 e) cooling of the product;
 f) optional calibration of the granules or microgranules;
 g) application of a gastro-resistant coating.

* * * * *